United States Patent
Lerchen et al.

[11] Patent Number: 6,156,754
[45] Date of Patent: Dec. 5, 2000

[54] GLYCOCONJUGATES OF MODIFIED CAMPTOTHECIN DERIVATIVES (A-OR B-RING LINKAGE)

[75] Inventors: Hans-Georg Lerchen; Karsten von dem Bruch, both of Leverkusen; Jörg Baumgarten; Michael Sperzel, both of Wuppertal, all of Germany

[73] Assignee: Bayer Aktiengesellschaft, Leverkusen, Germany

[21] Appl. No.: 09/269,314

[22] PCT Filed: Sep. 17, 1997

[86] PCT No.: PCT/EP97/05089

§ 371 Date: Mar. 24, 1999

§ 102(e) Date: Mar. 24, 1999

[87] PCT Pub. No.: WO98/14468

PCT Pub. Date: Apr. 9, 1998

[30] Foreign Application Priority Data

Sep. 30, 1996 [DE] Germany .............. 196 40 207

[51] Int. Cl.[7] .............. A61K 31/50; A61K 31/44; C07D 471/00; C07D 401/00
[52] U.S. Cl. .............. 514/253.02; 283/279; 546/48; 546/41; 544/361
[58] Field of Search .............. 546/41, 48; 514/185, 514/283, 279, 253.02; 544/361

[56] References Cited

U.S. PATENT DOCUMENTS

| | | |
|---|---|---|
| 4,943,579 | 7/1990 | Vishnuvajjala et al. . |
| 5,340,817 | 8/1994 | Wall et al. . |
| 5,646,159 | 7/1997 | Wall et al. . |
| 5,688,931 | 11/1997 | Nogusa et al. . |
| 5,837,673 | 11/1998 | Tsujihara et al. . |
| 5,892,043 | 4/1999 | Tsujihara et al. . |
| 5,955,100 | 9/1999 | Bosslet et al. . |

FOREIGN PATENT DOCUMENTS

| | | |
|---|---|---|
| 0 418 099 | 3/1991 | European Pat. Off. . |
| 0 624 377 A2 | 11/1994 | European Pat. Off. . |
| 0 640 622 | 3/1995 | European Pat. Off. . |
| 0 757 049 | 2/1997 | European Pat. Off. . |
| 0 781 781 | 7/1997 | European Pat. Off. . |
| 42 36 237 | 4/1994 | Germany . |
| WO0556585 | 1/1993 | WIPO ...................... 491/22 |
| WO 96/02546 | 2/1996 | WIPO . |

OTHER PUBLICATIONS

J. Am. Chem. Soc. 88, 3888 (1966), Wall et al.
Neoglycoconjugaates: Fundamentals and recent progresses Ubersichtsartikel Lee Y.C. and Lee, R. in Lectins and Cancer 1991, 53–69; edited by Gabius M.J. and Gabius S., Springer Verlag.
J. Med. Chem. 38 (1995), 395, Luzzio et al.

*Primary Examiner*—John Kight
*Assistant Examiner*—Binta Robinson
*Attorney, Agent, or Firm*—Norris, McLaughlin & Marcus, P.A.

[57] ABSTRACT

The present invention relates to glycoconjugates of camptothecin derivatives in which at least one carbohydrate component is linked via suitable spacers with the A or B ring of a camptothecin derivative. The invention furthermore relates to processes for preparing the compounds according to the invention and to their use as medicaments, in particular in connection with cancer.

10 Claims, No Drawings

GLYCOCONJUGATES OF MODIFIED CAMPTOTHECIN DERIVATIVES (A-OR B-RING LINKAGE)

This application is a 371 of PCT/EP97/05089 filed on Sep. 17, 1997.

The present invention relates to glycoconjugates of camptothecin derivatives in which at least one carbohydrate component is linked via suitable spacers with the A or B ring of a camptothecin derivative. The invention furthermore relates to processes for preparing the compounds according to the invention and to their use as medicaments, in particular in connection with cancers.

20(S)-Camptothecin is a pentacyclic alkaloid which was isolated in 1966 by Wall et al. (J.Am.Chem.Soc. 88, 3888 (1966)). It has a high antitumour activity potential in numerous in vitro and in vivo tests. Unfortunately, however, the promising potential failed to be realized in the clinic because of toxicity and solubility problems.

By opening of the E ring lactone and formation of the sodium salt, a water-soluble compound was obtained which is in a pH-dependent equilibrium with the ring-closed form. Here too, clinical studies have been unsuccessful until now.

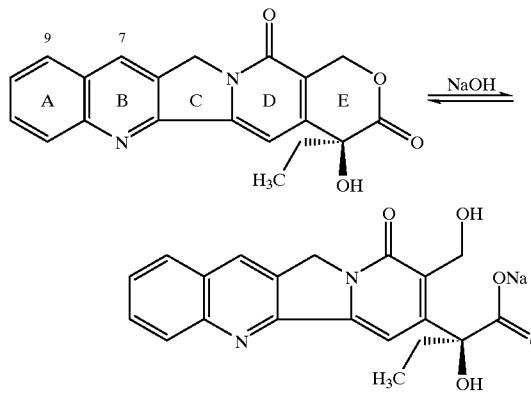

Approximately 20 years later, it was found that the biological activity is to be attributed to an enzyme inhibition of the topoisomerase I. Since then, the research activities have been increased again in order to find camptothecin derivatives which are more compatible and active in vivo.

To improve the water-solubility, salts of A ring- and B ring-modified camptothecin derivatives and of 20-O-acyl derivatives having ionizable groups have been described (Vishnuvajjala et al. U.S. Pat. No. 4943579). The latter prodrug concept was later also applied to modified camptothecin derivatives (Wani et al. WO 9602546). In vivo, however, the 20-O-acyl prodrugs described have a very short half-life and are very rapidly cleaved to give the parent structure.

Surprisingly, we have now found that the linkage of carbohydrate derivatives via suitable spacers on amino or hydroxyl groups which are connected to the A or B ring of camptothecin derivatives directly or via a spacer leads to a class of compounds having highly interesting properties:

The conjugates obtained in this manner have high in vitro activity against tumour cell lines and tumour xenografts.

Compared with the underlying toxophores, they have markedly higher tolerability and tumour selectivity and improved solubility, in particular in aqueous media.

In vivo, they exhibit excellent therapeutic activity over several dose stages.

In extracellular medium and in blood, they are considerably more stable than the 20-O-acyl prodrugs of camptothecin described in the literature.

The present invention relates to compounds of the general formula (I)

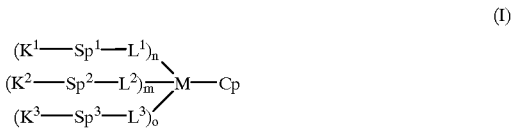

in which n, m and o in each case represent the number 0 or 1 and n+m+o is $\geq 1$ where Cp represents a camptothecin derivative of the formulae

[A]

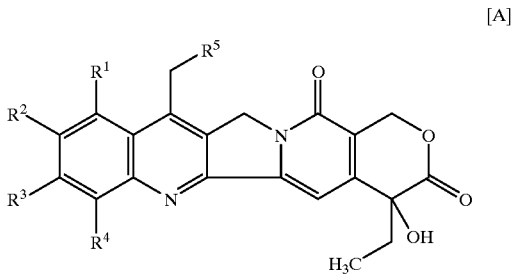

in which $R^1$, $R^2$, $R^3$ and $R^4$ independently of one another may represent hydrogen, alkyl having up to 3 carbon atoms, halogen, amino, hydroxyl or nitro or $R^2$ and $R^3$ together represent a group of the formula

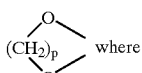 where p may have the values 1 or 2 and
$R^5$ represents —O—*, —NH* or

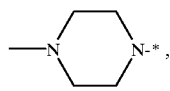

or represents —*$NR^6$, in which $R^6$ represents arylmethyl or hetarylmethyl,

[B]

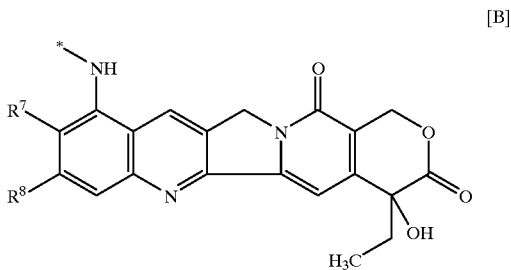

in which
$R^7$ and $R^8$ are as defined for $R^2$ and $R^3$ and may be identical or different to these,

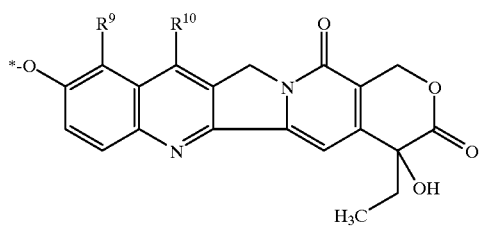

[C]

in which
R$^9$ represents hydrogen or —CH$_2$—N(CH$_3$)$_2$ and
R$^{10}$ represents hydrogen or ethyl,

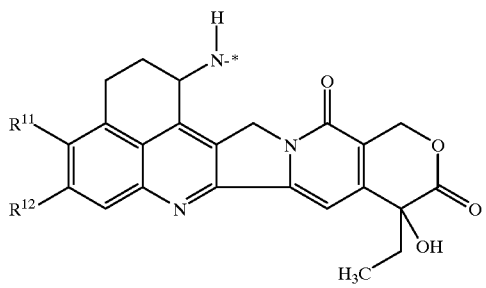

[D]

in which
R$^{11}$ and R$^{12}$ are as defined for R$^2$ and R$^3$ and may be identical or different to these, or

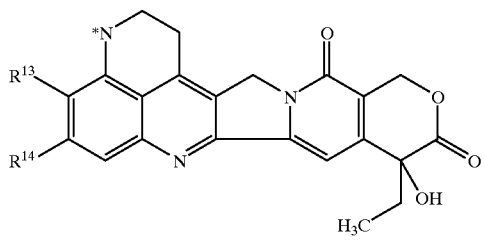

[E]

in which
R$^{13}$ and R$^{14}$ are as defined for R$^2$ and R$^3$ and may be identical or different to these, where Cp is attached to M via the bonds labelled *, M represents a bridge grouping whose main chain includes up to 21 atoms in linear order, L$^1$, L$^2$ and L$^3$ independently of one another each represent linker groupings customarily used in glycoconjugate chemistry, (see review article Lee Y.C. and Lee, R. in Lectins and Cancer 1991, 53–69; edited by Gabius M. J. and Gabius S., Springer Verlag), Sp$^1$, Sp$^2$ and Sp$^3$ independently of one another each represent arylene having up to 10 carbon atoms or represent alkylene having up to 8 carbon atoms which are in each case optionally substituted, and K$^1$, K$^2$ and K$^3$ independently of one another each represent a radical of the formula (II)

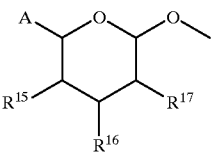

(II)

in which
A represents methyl, hydroxymethyl, alkoxymethyl having up to 6 carbon atoms, acyloxymethyl having up to 6 carbon atoms or a radical of the formula —CH$_2$—B in which B represents a radical of the formula (II), R$^{15}$, R$^{16}$ and R$^{17}$ independently of one another each represent hydrogen, hydroxyl, optionally hydroxyl-substituted alkoxy having up to 6 carbon atoms, amino which is optionally substituted by alkyl or acyl having up to 6 carbon atoms, halogen, sulphate or a group of the formula

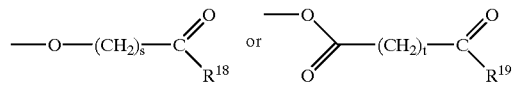

in which
R$^{18}$ and R$^{19}$ independently of one another each represent hydroxyl or alkoxy having up to 6 carbon atoms or represent amino which is optionally substituted by alkyl having up to 6 carbon atoms, and s and t independently of one another may each have the values 0, 1, 2, 3 or 4, in particular the values 1, 2, 3 or 4, or R$^{15}$, R$^{16}$ and R$^{17}$ independently of one another each represent a radical of the formula (II) or two of the radicals R$^{15}$, R$^{16}$, R$^{17}$ together represent an epoxy group, and their isomers, isomer mixtures and salts.

Unless stated otherwise in the context of the invention, the term "alkyl group" includes straight-chain, branched, cyclic and cycloalkyl-radical-containing alkyl radicals. Correspondingly, this definition also applies to all the other radicals containing alkyl groups, such as, for example, alkoxy, acyl, etc.

The terms arylmethyl and hetarylmethyl given in the definition of R$^6$ may represent, for example, phenylmethyl or pyridylmethyl.

Preference is given to compounds of the general formula (I) in which K$^1$, K$^2$ and K$^3$ independently of one another may each represent a radical of the formula (II) where A represents methyl, hydroxymethyl, methoxymethyl or acetoxymethyl, R$^{15}$ represents hydrogen, hydroxyl, methoxy or a group of the formula

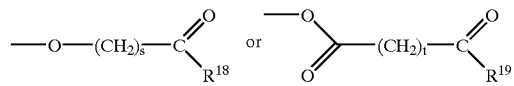

in which
s and t independently of one another may each have the values 1 or 2 and R$^{18}$ and R$^{19}$ independently of one another each represent hydroxyl or alkoxy having up to 4 carbon atoms, or $R^{15}$ represents a radical of the formula (II),
$R^{16}$ represents hydrogen, hydroxyl, halogen, alkoxy having up to 4 carbon atoms, sulphate or a group of the formula

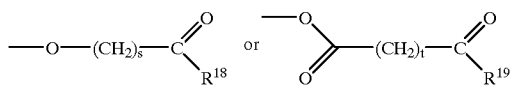

in which
s and t independently of one another may each have the values 1 or 2 and
$R^{18}$ and $R^{19}$ independently of one another each represent hydroxyl or alkoxy having up to 4 carbon atoms or represent amino which is optionally substituted by alkyl having up to 4 carbon atoms,
$R^{17}$ represents hydroxyl, alkoxy having up to 4 carbon atoms which is optionally substituted by hydroxyl, amino which is optionally substituted by alkyl or acyl having up to 4 carbon atoms, or a group of the formula

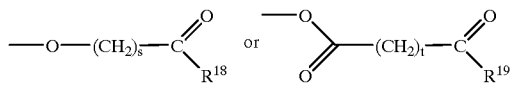

in which
s and t independently of one another may each have the values 1 or 2 and
$R^{18}$ and $R^{19}$ independently of one another each represent hydroxyl or alkoxy having up to 4 carbon atoms, or in which
$R^{15}$ and $R^{16}$ together represent an epoxy group, and their isomers, isomer mixtures and salts.

Very particularly preferably, $K^1$, $K^2$ and $K^3$ independently of one another each represent a radical of the formula (II), where
A represents methyl, hydroxymethyl, methoxymethyl or acetoxymethyl,
$R^{15}$ and $R^{17}$ each represent a hydroxyl group, and
$R^{16}$ represents hydrogen, hydroxyl, halogen, alkoxy having up to 4 carbon atoms, sulphate or a group of the formula

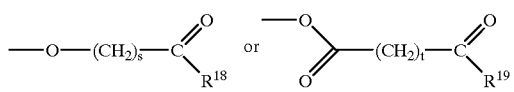

in which
s and t independently of one another may each have the values 1 or 2 and
$R^{18}$ and $R^{19}$ independently of one another each represent hydroxyl or alkoxy having up to 4 carbon atoms or represent amino which is optionally substituted by alkyl having up to 4 carbon atoms.

According to a particularly preferred embodiment, the carbohydrate building blocks $K^1$, $K^2$ and/or $K^3$ include in each case at most two monosaccharide building blocks.

Preference is furthermore given to compounds of the general formula (I) in which $Sp^1$, $Sp^2$ and/or $Sp^3$ independently of one another may each represent arylene having up to 10 carbon atoms which is attached to in each case one group $K^1$ and/or $K^2$ or $K^3$ and $L^1$ and/or $L^2$ or $L^3$ and which is optionally also mono- or polysubstituted by hydroxyl, carboxyl, carboxyalkyl having up to 4 carbon atoms, nitro, cyano, halogen, alkyl having up to 4 carbon atoms, halogenoalkyl having up to 4 carbon atoms or by alkoxy having up to 4 carbon atoms, and their isomers, isomer mixtures and salts.

Not taking $K^1$, $K^2$ or $K^3$ and $L^1$, $L^2$ or $L^3$ into account, $Sp^1$, $Sp^2$ and/or $Sp^3$ are particularly preferably unsubstituted or optionally substituted by halogen, nitro, alkyl having up to 4 carbon atoms, alkoxy having up to 2 carbon atoms, —$OCF_3$ and/or $CF_3$.

Very particularly preferably, $Sp^1$, $Sp^2$ and/or $Sp^3$ carry no other substituents apart from a group $K^1$, $K^2$ or $K^3$ and a group $L^1$, $L^2$ or $L^3$ each, which are attached para to one another.

Preference is furthermore given to compounds of the general formula (I)
in which
$L^1$, $L^2$ and $L^3$ independently of one another each represent

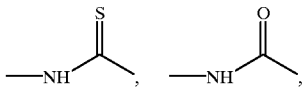

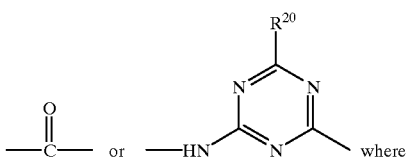

$R^{20}$ represents chlorine or represents hydroxyalkylamino having up to 6 carbon atoms.
Particularly preferably, $L^1$, $L^2$ and $L^3$ each represent

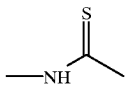

Preference is furthermore given to compounds of the general formula (I) in which M represents a peptide which is attached to $L^1$, $L^2$ and/or $L^3$ via an amino function, is attached to Cp via an acyl function and whose amino acid building blocks may optionally carry protective groups. Particular preference is given to mono-, di- and tripeptides, in particular to mono- and dipeptides.

The amino acid building blocks are preferably selected from the group consisting of glycyl, alanyl, valyl, leucyl, lysyl, seryl, glutamyl, threonyl, asparagyl, isoleucyl, diaminopropionyl, diaminobutyryl, histidyl, arginyl and/or ornithyl.

Particular preference is given to the amino acid building blocks glycyl, alanyl, valyl, leucyl, lysyl, seryl, asparagyl, histidyl and/or glutamyl.

The compounds according to the invention may be present in stereoisomeric forms, for example as enantiomers or diastereomers, or as mixtures thereof, for example as a racemate. The invention relates both to the pure stereoisomers and to their mixtures.

If required, mixtures of stereoisomers can be separated into the stereoisomerically uniform components in a manner known per se, for example by chromatography or by crystallization processes.

Owing to restricted rotation, the compounds according to the invention may occur in the form of rotational isomers or as their mixtures. The invention relates both to the pure rotational isomers and to their mixtures.

Mixtures of rotational isomers can optionally, if required, be separated into the uniform components using known methods, for example by chromatography (for example HPLC) or by crystallization processes. This can be done not only at the end stage of the glycoconjugates, but also, if appropriate, at intermediate stages. If appropriate, the rotamerically pure end products can be prepared from rotamerically pure intermediates by conducting the synthesis in an appropriate manner.

The stereochemistry at the anomeric centre of the carbohydrate building blocks $K^1$, $K^2$ and/or $K^3$ may be α or β. The stereochemistry at the other centres may result in the gluco, manno, galacto, gulo, rhamno or fuco configuration.

The amino acid building blocks may, just like the carbohydrate building blocks, in each case be present in the D or in the L form.

The camptothecin building block Cp can be present in the 20-(R) or in the 20-(S) configuration or as a mixture of these two stereoisomeric forms. Preference is given to the 20-(S) configuration.

Preferred examples of the camptothecin building block are:

[A1]
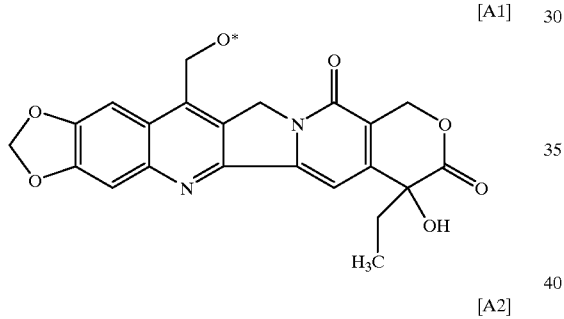

[A2]
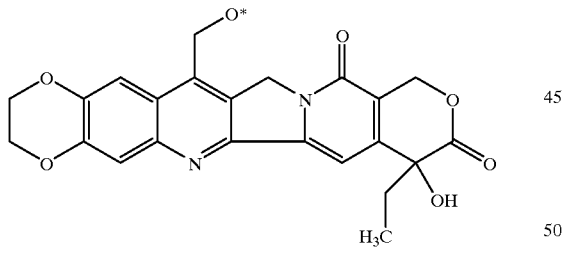

[A3]
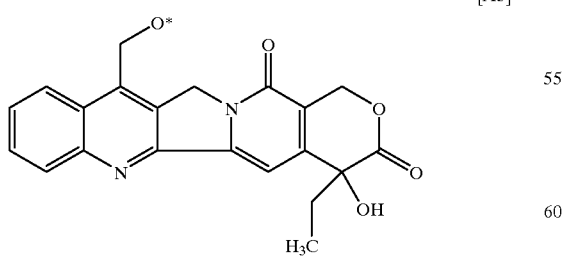

-continued

[A4]
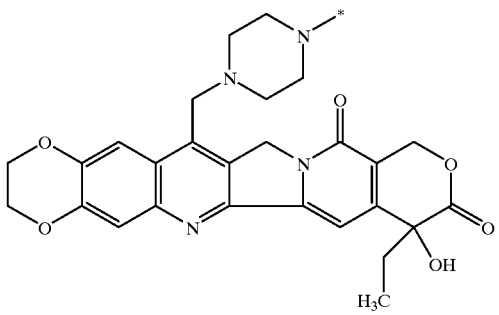

[A5]
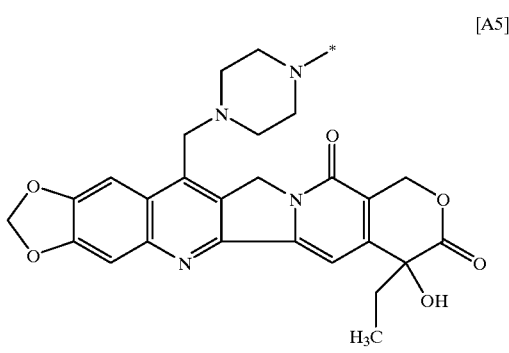

[A6]
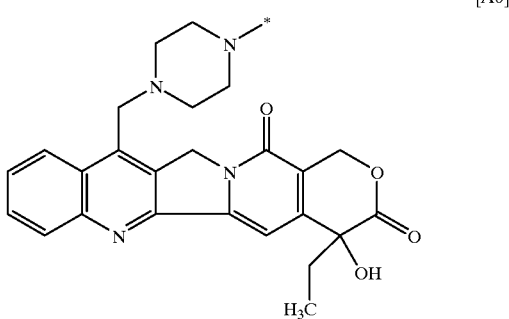

[B1]
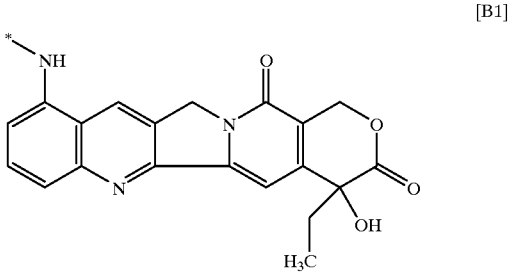

[B2]
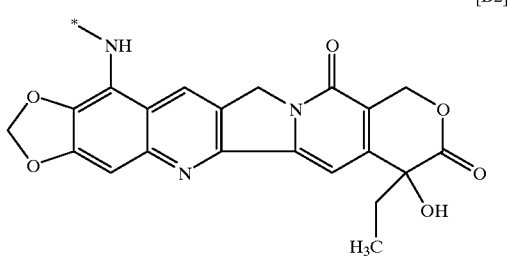

-continued

[B3]

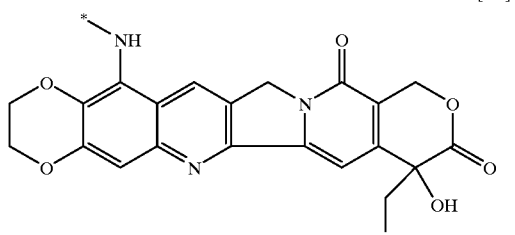

[C1]

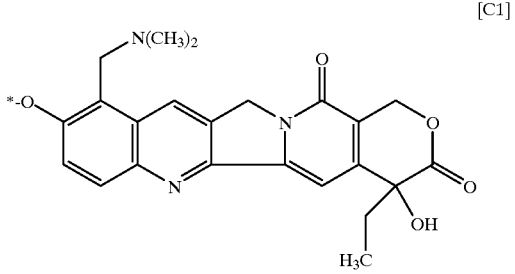

[C2]

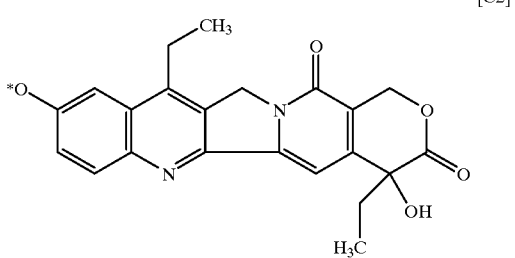

[D1]

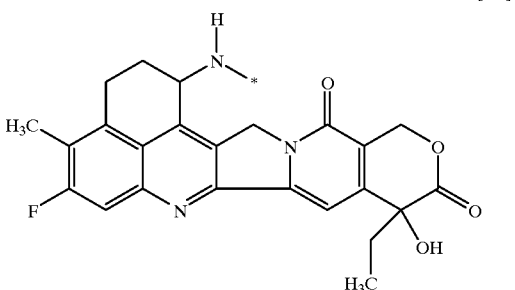

[D2]

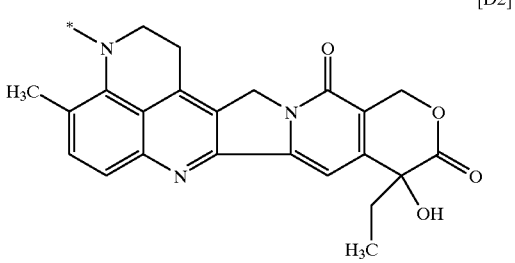

Among these camptothecin building blocks which are mentioned by way of example, particular preference is given to: [A1], [A3], [A4], [B1], [B2], [D1].

By combining the preferred or particularly preferred meanings given for the individual radicals, corresponding very particularly preferred compounds of the general formula (I) result.

The compounds according to the invention may also be present in the form of their salts. In general, salts with organic or inorganic bases or acids and also inner salts may be mentioned here.

The acids which can be adducted preferably include hydrohalic acids, such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids, such as, for example, acetic acid, trifluoroacetic acid, maleic acid, malonic acid, oxalic acid, gluconic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

Physiologically acceptable salts may also be the metal or ammonium salts of the compounds according to the invention which have a free carboxyl group. Particular preference is given, for example, to sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or phenethylamine.

The glycoconjugates according to the invention can be prepared, for example, by linkage of amino- or hydroxyl-modified camptothecin derivatives with activated carboxyl components, which for their part, for example, can be moieties of protected amino acids, peptides or carbohydrate-modified peptides.

The invention thus furthermore relates to a process for preparing compounds of the general formula (I), characterized in that compounds of the general formula (III)

$$Cp—H \qquad (III)$$

in which Cp is as defined above and the hydrogen atom is located on the positions labelled *, are reacted with an activated carboxyl component Ma which corresponds to the radical M defined above and optionally carries protective groups, in a suitable solvent, if appropriate in the presence of a base, by customary methods, one, more than one or all protective groups of M are, if appropriate, selectively removed by known methods and the product is reacted with compounds of the general formula (IV)

$$K^1—Sp^1—L^1a \qquad (IV)$$

in which $K^1$ and $Sp^1$ are each as defined above and $L^1a$ represents a reactive precursor of the group $L^1$, where the protective groups are, if appropriate, selectively removed and various groups $K^2—Sp^2—L^2—$ and $K^3—Sp^3—L^3—$ can be introduced stepwise in a comparable manner or that, if M is a peptide, a first amino acid radical is introduced in a comparable manner by customary methods in the form of a corresponding activated carboxyl component which optionally carries protective groups, protective groups are, if appropriate, removed, amino acid radicals which optionally carry protective groups are furthermore attached, protective groups are, if appropriate, removed again, radicals of the formulae $K^1—Sp^1—L^1—$, $K^2—Sp^2—L^2—$ and/or $K^3—Sp^3—L^3—$ are introduced as stated above and, if required, protective groups are removed.

The reactions can be carried out under various pressure and temperature conditions. for example 0.5 to 2 bar, and −30 to +100° C., in suitable solvents such as dimethylformamide (DMF), tetrahydrofuran (THF), dichloromethane, chloroform, lower alcohols, acetonitrile, dioxane, water or in mixtures of the solvents mentioned. In general, reactions in DMF or THF/dichloromethane at normal pressure and at a temperature of from 0 to 60° C., in particular at approximately room temperature, are preferred.

For the activation of the carboxyl groups, possible coupling reagents are those known in peptide chemistry such as described, for example, in Jakubke/Jeschkeit: Aminosäuren, Peptide, Proteine [Amino Acids, Peptides, Proteins]; Verlag Chemie 1982 or Tetrahedr. Lett. 34, 6705 (1993). Acyl chlorides, N-carboxylic anhydrides or mixed anhydrides, for example, are preferred.

Furthermore suitable for the activation of the carboxyl groups is the formation of adducts with carbodiimides, e.g. N,N'-diethyl-, N,N'-diisopropyl-, N,N'-dicyclohexylcarbodiimide, N-(3-dimethylaminopropyl)-N'-ethyl-carbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluoro-phosphate, 1-hydroxybenzotriazole or N-hydroxysuccinimide.

Bases employed can be, for example, triethylamine, ethyldiisopropylamine, pyridine, N,N-dimethylaminopyridine or others.

Protective groups employed for any third functions of the amino acids or non-linkage positions in the camptothecin moiety can be the protective groups known in peptide chemistry, for example of the urethane, alkyl, acyl, ester or amide type.

Amino protective groups in the context of the invention are the customary amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl (Boc), allyloxycarbonyl, vinyloxycarbonyl, 3,4,5-trimethoxybenzyloxy-carbonyl, 2,2,2-trichloroethoxycarbonyl, 2,2,2-trichloro-tert-butoxycarbonyl, menthyloxycarbonyl, 4-nitrophenoxycarbonyl, fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl or 2-nitrophenylsulphenyl. The Fmoc group and the Boc group are particularly preferred.

Preferred carboxyl protective groups are linear or branched $C_1$-to $C_4$-alkyl esters.

The camptothecin derivatives linked with a bridge grouping M can be modified with carbohydrate radicals using various methods and linker groups. Preference is given, for example, to converting p-aminophenyl glycosides into isothiocyanates and linkage, for example, with amino groups. Furthermore, it is also easily possible to couple carboxyalkyl or aminoalkyl glycosides with amino or carboxyl groups.

The removal of protective groups in appropriate reaction steps can be carried out, for example, by the action of acid or base, hydrogenolytically or reductively in another manner.

Biological Testing

1. Growth Inhibition Test for the Determination of the Cytotoxic Properties

The human large intestine cell lines SW 480 and HT 29 (ATCC No. CCL 228 and HBT 38) and the mouse melanoma cell line B 16 F 10 were grown in Roux dishes in RPMI 1640 medium with addition of 10% FCS. They were then trypsinized and taken up in RPMI plus 10% FCS to a cell count of 50,000 cells/ml. 100 μl of cell suspension/well were added to a 96 microwell plate and incubated for 1 day at 37° C. in a $CO_2$ incubator. A further 100 μl of RPMI Medium and 1 μl of DMSO containing the test substances were then added. The growth was checked after day 3 and day 6. To this end, 40 μl of MTT solution (3-(4,5-dimethylthiazol-2-yl)-2,5-diphenyl-tetrazolium bromide) having a starting concentration of 5 mg/ml of $H_2O$ were added to each microwell. Incubation was carried out for 5 hours in a $CO_2$ incubator at 37° C. The medium was then aspirated and 100 μl of i-propanol/well were added. After shaking for 30 min with 100 μl of $H_2O$, the extinction was measured at 540 nm using a Titertek Multiscan MCC/340 (Flow).

The cytotoxic action is indicated in Table 1 as the $IC_{50}$ value (dose which inhibits the cell growth to 50% of the cell growth of the control) in each case for the SW 480 and HT 29 and B16F10 cell lines:

TABLE 1

| Example | $IC_{50}$/nM SW 480 | $IC_{50}$/nM HT 29 | $IC_{50}$/nM B16F10 |
|---|---|---|---|
| 1.1 | 0.015 | 0.025 | 0.18 |
| 1.3 | 0.04 | 0.03 | n.d. |
| 1.4 | 0.03 | 0.04 | 0.2 |
| 2.1 | 0.2 | 0.06 | 2 |
| 3.1 | 0.08 | 0.06 | 0.5 |
| 3.3 | 0.25 | 0.1 | n.d. |
| 3.5 | 0.3 | 0.3 | n.d. |
| 4.1 | 0.03 | 0.04 | n.d. |

2. Haematopoietic Activity of Glycoconjugates in Comparison with the Underlying Active Compound Materials and Methods Bone marrow cells are washed out of mice femurs. $10^5$ cells are incubated at 37° C. and 7% $CO_2$ in McCoy 5A medium (0.3% agar) together with recombinant murine GM-CSF (Genzyme; stem cell colony formation) and the substances ($10^{-4}$ to 100 μg/ml). 7 days later, the colonies (<50 cells) and clusters (17–50 cells) are counted.

Results

As shown in Tab. 2 with reference to Example 2.1, the glycoconjugates investigated show, compared with the underlying active compound, an inhibition of the bone marrow stem cell proliferation which is reduced approximately by the factor 100.

TABLE 2

| Example | $IC_{50}$ [μg/ml] |
|---|---|
| 2.1.a | 0.0016 |
| 2.1 | 0.17 |

3. In Vivo Inhibition of Tumour Growth in the Nude Mouse Model

Material

For all in vivo experiments for investigation of the inhibition of tumour growth athymic nude mice (NMRI nu/nu strain) were used. The selected large-cell lung carcinoma LXFL 529 was grown by serial passage in nude mice. The human origin of the tumour was confirmed by isoenzymatic and immunohistochemical methods.

Experimental Set-up

The tumour was implanted subcutaneously into both flanks of 6 to 8 week old nu/nu nude mice. The treatment was started, depending on the doubling time, as soon as the tumours had reached a diameter of 5–7 mm. The mice were assigned to the treatment group and the control group (5 mice per group with 8–10 assessable tumours) by randomization. The individual tumours of the control group all grew progessively.

The size of the tumours was measured in two dimensions by means of a slide gauge. The tumour volume, which correlated well with the cell count, was then used for all evaluations. The volume was calculated according to the formula "length×breadth×breadth/2" ([a×b²]/2, a and b represent two diameters at right angles).

The values of the relative tumour volume (RTV) were calculated for each individual tumour by dividing the tumour size on day X with the tumour size on day 0 (at the time of randomization). The mean values of the RTV were then used for the further evaluation.

The inhibition of the increase of the tumour volume (tumour volume of the test group/control group, T/C, in per cent) was the final measured value.

Treatment

The administration of the compounds was carried out intraperitoneally (i.p.) on day 1, 2 and 3 after randomization.

Results

Using the compound from Example 1.1, the therapeutic efficacy of the glycoconjugates according to the invention is compared with the large-cell human lung tumour xenograft LXFL 529. In the case of the maximum tolerable dose (MTD), at ½ MTD and at ¼ MTD, the therapy leads to a complete remission of the tumour.

TABLE 3

| Therapy | Dose [mg/kg/day] | Survival time [days] | Number of tumours | Relative tumour volume on day 14 [% of day 0] | Relative body weight on day 7 [% of day 0] |
|---|---|---|---|---|---|
| Control group | — | >21 >21<br>>21 >21<br>>21 | 10 | 691 | 102 |
| 1.1 | 12.5 (MTD) | >21 >21<br>>21 >21<br>>21 | 9 | 0.1 | 72 |
| 1.1 | 6.25 | >21 >21<br>>21 >21<br>>21 | 10 | 0.1 | 93 |
| 1.1 | 3.125 | >21 >21<br>>21 >21<br>>21 | 9 | 0.1 | 93 |

Both in vitro and in vivo, the compounds according to the invention have a surprisingly strong antitumour activity against various tumours, in particular those of the lungs and the large intestine, in combination with a high selectivity compared to non-malignant cells.

They are therefore suitable for treating cancers, in particular cancer of the lung and the large intestine.

The present invention includes pharmaceutical preparations which, in addition to non-toxic, inert pharmaceutically suitable excipients, contain one or more compounds according to the invention or which consist of one or more active compounds according to the invention, and processes for the production of these preparations.

The active compound(s) can optionally be present in one or more of the excipients indicated above and also in microencapsulated form.

The therapeutically active compounds should preferably be present in the abovementioned pharmaceutical preparations in a concentration of from approximately 0.1 to 99.5, preferably from approximately 0.5 to 95, % by weight of the total mixture.

Apart from the compounds according to the invention, the abovementioned pharmaceutical preparations can also contain further pharmaceutically active compounds.

In general, it is proven advantageous both in human and in veterinary medicine to administer the active compound(s) according to the invention in total amounts of from approximately 0.5 to approximately 500, preferably 5 to 100, mg/kg of body weight every 24 hours, if appropriate in the form of several individual doses, to achieve the desired results. An individual dose contains the active compound(s) according to the invention preferably in amounts of from approximately 1 to approximately 80, in particular 3 to 30, mg/kg of body weight.

EXAMPLES

Carbohydrate Starting Materials

Example I.1 p-Aminophenyl 3-O-methyl-β-L-fucopyranoside

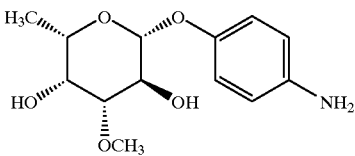

I.1.a) p-Nitrophenyl 3-O-methyl-β-L-fucopyranoside 6 g (21 mmol) of p-nitrophenyl β-L-fucopyranoside in 300 ml of absol. methanol are treated with 7.84 g (31.5 mmol) of dibutyl tin oxide and heated under reflux for 2 h. The mixture is then concentrated, and the residue is dried and then taken up in 300 ml of DMF. After addition of 15.7 ml of methyl iodide, the batch is stirred at 70° C. for 40 h. The solvent is removed under reduced pressure and the residue is taken up in 300 ml of dichloromethane. The suspension is filtered, and the solution that remains is concentrated again and subjected to flash chromatography (dichloromethane/methanol 99:1). The concentration gives 3.82 g (61%) of the target product.

I.1) p-Aminophenyl 3-O-methyl-β-L-fucopyranoside 3.81 g (12.73 nmmol) of p-nitrophenyl 3-O-methyl-β-L-fucopyranoside are dissolved in methanol and, after addition of platinum dioxide, hydrogenated in a hydrogen atmosphere at a slight overpressure. After filtering off the catalyst and precipitating with ether, 3 g (88%) of the target product are obtained. [TLC: dichloromethane/methanol 9:1 $R_f$=0.53].

Example I.2 p-Aminophenyl 3-O-carboxymethyl-β-L-fucopyranoside

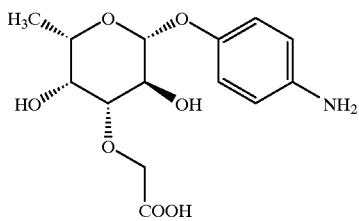

I.2.a) p-Nitrophenyl 3-O-methoxycarbonylmethyl-β-L-fucopyranoside 1 g (3.5 mmol) of p-nitrophenyl β-L-fucopyranoside and 1.3 g (5.2 mmol) of dibutyl tin oxide in 50 ml of methanol are heated under reflux for 2 h. The solution is concentrated, the residue is taken up in 50 ml of dioxane, admixed with 2 ml of methyl bromoacetate and 100 mg of tetrabutylammonium iodide, and the mixture is heated under reflux for 16 h. The solvent is evaporated off and the product is purified by flash chromatography (dichloromethane/methanol 99:1). After concentrating the appropriate fractions and precipitating from methanol/ether, 455 mg (37%) of the target compound are obtained.

I.2) p-Aminophenyl 3-O-carboxymethyl-β-L-fucopyranoside 282 mg (0.79 mmol) of p-nitrophenyl 3-methoxycarbonylmethyl-β-L-fucopyranoside are dissolved in 20 ml of methanol and admixed with 440 μl of an aqueous 2N lithium hydroxide solution. The mixture is stirred at room temperature for 2 h and then adjusted to pH 3 using acidic ion exchanger SC108 and filtered. 250 mg of palladium on activated carbon are added to the filtrate. The mixture is subsequently hydrogenated for 1.5 h using a slight hydrogen overpressure, and the catalyst is separated off and washed with methanol. Concentration, taking up in water and freeze drying gives the target product (212 mg) in 86% yield. [TLC: acetonitrile/water/glacial acetic acid 5:1:0.2 $R_f$=0.24]

The following derivatives, for example, can be used as further carbohydrate building blocks:

p-aminophenyl β-L-fucopyranoside
p-aminophenyl 2-O-methyl-β-L-fucopyranoside
p-aminophenyl 2-O-hydroxyethyl-β-L-fucopyranoside
p-aminophenyl 4-O-methyl-β-L-fucopyranoside
p-aminophenyl 3-O-methyl-α-L-fucopyranoside
p-aminophenyl 3-O-n-propyl-β-L-fucopyranoside
p-aminophenyl 3-deoxy-β-L-fucopyranoside
p-aminophenyl 3,4-dideoxy-β-L-fucopyranoside
p-aminophenyl 3,4-epoxy-β-L-fucopyranoside
p-aminophenyl 4-deoxy-β-L-fucopyranoside
p-aminophenyl 3-O-methoxycarbonylmethyl-β-L-fucopyranoside
p-aminophenyl 3-O-hydroxyethyl-β-L-fucopyranoside
p-aminophenyl 2-O-carboxymethyl-β-L-fucopyranoside
p-aminophenyl 3-O-succinyl-β-L-fucopyranoside
p-aminophenyl 3,4-di-O-methyl-β-L-fucopyranoside
p-aminophenyl 3-O-carbamoylmethyl-β-L-fucopyranoside
p-aminophenyl α-L-rhamnopyranoside
p-aminophenyl β-D-galactopyranoside
p-aminophenyl 2-O-methyl-β-D-galactopyranoside
p-aminophenyl 3-O-methyl-β-D-galactopyranoside
p-aminophenyl 4-O-methyl-β-D-galactopyranoside
p-aminophenyl 6-O-methyl-β-D-galactopyranoside
p-aminophenyl 2,3-di-O-methyl-β-D-galactopyranoside
p-aminophenyl 2,4-di-O-methyl-β-D-galactopyranoside
p-aminophenyl 2,6-di-O-methyl-β-D-galactopyranoside
p-aminophenyl 3,4-di-O-methyl-β-D-galactopyranoside, acetate
p-aminophenyl 3,6-di-O-methyl-β-D-galactopyranoside
p-aminophenyl 4,6-di-O-methyl-β-D-galactopyranoside
p-aminophenyl 2,3,4-tri-O-methyl-β-D-galactopyranoside
p-aminophenyl 2,3,6-tri-O-methyl-β-D-galactopyranoside
p-aminophenyl 2,4,6-tri-O-methyl-β-D-galactopyranoside
p-aminophenyl 3,4,6-tri-O-methyl-β-D-galactopyranoside
p-aminophenyl 3-deoxy-β-D-galactopyranoside
p-aminophenyl 3,4-dideoxy-β-D-galactopyranoside
p-aminophenyl 6-O-acetyl-β-D-galactopyranoside
p-aminophenyl 3-O-methoxycarbonylmethyl-β-D-galactopyranoside
p-aminophenyl 3-O-carboxymethyl-β-D-galactopyranoside, sodium salt
p-aminophenyl 3-O-carbamoylmethyl-β-D-galactopyranoside
p-aminophenyl 3-O-(N-methyl-carbamoylmethyl)-β-D-galactopyranoside
p-aminophenyl α-D-mannopyranoside
p-aminophenyl 3-O-methyl-α-D-mannopyranoside
p-aminophenyl 2,3-di-O-methyl-α-D-mannopyranoside
p-aminophenyl 3-O-methoxycarbonylmethyl-α-D-mannopyranoside
p-aminophenyl 3-O-carboxymethyl-α-D-mannopyranoside
p-aminophenyl 3-O-carbamoylmethyl-α-D-mannopyranoside
p-aminophenyl 4-O-(β-D-galactopyranosyl)-β-D-glucopyranoside
p-aminophenyl 4-O-(3'-sulphate-β-D-galactopyranosyl)-β-D-glucopyranoside, sodium salt
p-aminophenyl 4-O-(3'-O-methyl-β-D-galactopyranosyl)-β-D-glucopyranoside
p-aminophenyl 2-O-methyl-4-O-(3'-O-methyl-β-D-galactopyranosyl)-β-D-glucopyranoside
p-aminophenyl 4-O-(3',4'-di-O-methyl-β-D-galactopyranosyl)-β-D-glucopyranoside The synthesis of the following carbohydrate building blocks has already been described in EP 501 250:
Carboxymethyl β-L-fucopyranoside
5-Carboxypentyl β-L-fucopyranoside
These two building blocks can be linked with peptide conjugates in the manner described in EP 501 250.
Glycoconjugates

Example 1.1

7-{N$^α$,N$^ε$-bis-[O-(3-O-Methyl-β-L-fucopyranosyl)-4-hydroxy-phenylaminothiocarbonyl]-L-lysyl-L-alanyloxymethyl}-camptothecin

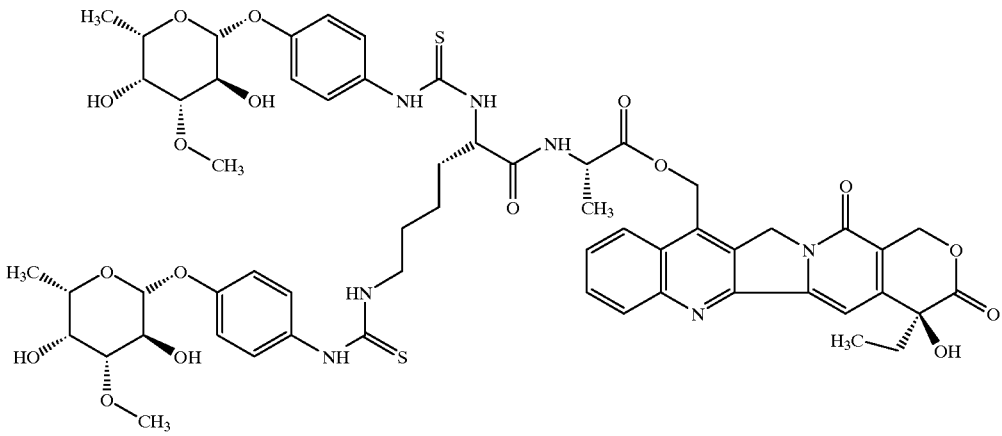

1.1.a) 7-Hydroxymethyl-camptothecin

This compound is prepared in accordance with the instructions of Miyasaka et al. (Chem. Pharm. Bull. 39 (1991) 2574).

1.1.b) 7-(L-Alanyloxymethyl)-camptothecin, trifluoroacetate 1 g (2.64 mmol) of 7-hydroxymethyl-camptothecin is dissolved in 100 ml of DMF, then 100 mg of 4-N,N-dimethylaminopyridine and 1.5 equivalents of N-tert-butyoxycarbonyl-L-alanine-N-carboxylic anhydride are added, and the suspension is stirred at room temperature for 16 h. It is concentrated and the residue is purified by flash chromatography on ethyl acetate/petroleum ether 1:1 and subsequently 1.5:1. The purified material is taken up in 30 ml of dichloromethane, and 5 ml of trifluoroacetic acid are added at 0° C. After 30 minutes of stirring, the mixture is concentrated and the amino-deblocked product is precipitated from dichloromethane/ether. It is subsequently lyophilized from dioxane/water. The target compound is obtained in a total yield of 59%. [FAB-MS: m/z=450=M+H].

1.1.c) 7-(L-Lysyl-L-alanyloxymethyl)-camptothecin, bis-trifluoroacetate 200 mg of the conjugate from Example 1.1.b are added to a solution of 150 mg (1.2 eq.) of $N^\alpha,N^\epsilon$-bis-(tert-butoxycarbonyl)-L-lysine, 88 mg of N-hydroxybenzotriazole and 100 mg of N-ethyl-N'-(3-dimethylaminopropyl)carbodiimide hydrochloride in 20 ml of dimethylformamide and the mixture is stirred at room temperature for one hour. It is then concentrated, the residue is taken up in dichloromethane, and the mixture is extracted three times with water. The organic phase is dried and concentrated and the residue is precipitated from methanol/ether. Subsequently, the product obtained is taken up in 15 ml of dichloromethane, 1 ml of trifluoroacetic acid is added at 0° C., and the mixture is stirred at room temperature for one hour. Then a further 1 ml of trifluoroacetic acid is added and stirring is carried out for a further hour. Concentration of the mixture and precipitation of the residue from dichloromethane/ether gives the target compound in a yield of 65%. [TLC: acetonitrile/water/glacial acetic acid 10:5:3 $R_f$=0.44].

1.1) 7-{$N^\alpha,N^\epsilon$-bis-[O-(3-O-Methyl-β-L-fucopyranosyl)-4-hydroxy-phenylaminothiocarbonyl]-L-lysyl-L-alanyloxymethyl}-camptothecin Thiophosgene (0.5 mmol) is added with stirring to a solution of Compound I.1 (0.35 mmol) in dioxane/water 1:1 (15 ml). After 10 minutes, 4 equivalents of ethyl diisopropylamine are added, then the mixture is concentrated under reduced pressure and the residue is dried for 1 h under an oil pump vacuum. The isothiocyanate which is obtained is dissolved in absolute dimethylformamide (10 ml), and compound 1.1.c (0.15 mmol) and 4 equivalents of ethyldiisopropylamine are added. The mixture is stirred at room temperature for 16 h and then concentrated under reduced pressure and the residue is stirred with 20 ml of water. The mixture is filtered with suction and the residue is taken up in dichloromethane/methanol and precipitated from ether. Reprecipitation gives the target product in a yield of 61%. [TLC: acetonitrile/water 10:1 $R_f$=0.45] [FAB-MS: m/z=1200=M+H].

Example 1.2

7-{$N^\alpha$-[O-(3-O-Carboxymethyl-β-L-fucopyranosyl)-4-hydroxy-phenylamino-thiocarbonyl]-L-lysyl-L-alanyloxymethyl}-camptothecin, hydrochloride

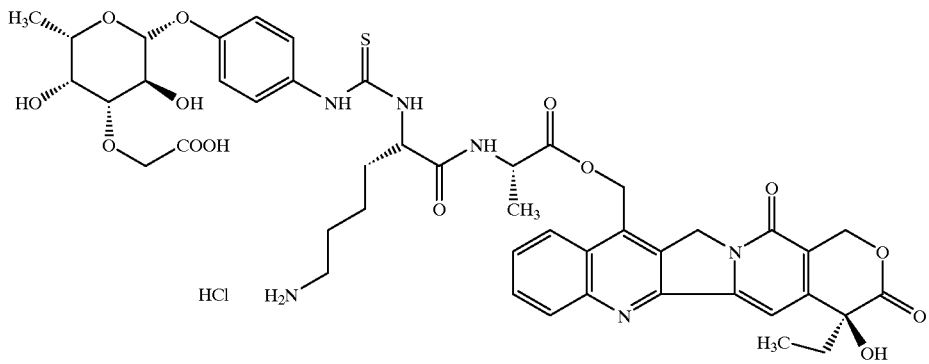

1.2.a) 7-[N^ε-(Fluorenyl-9-methoxycarbonyl)-L-lysyl-L-alanyloxymethyl]-)camptothecin, trifluoroacetate The conjugate from Example 1.1.b is coupled with N^α-(tert-butoxycarbonyl)-N^ε-(fluorenyl-9-methoxycarbonyl)-L-lysine in accordance with standard procedure and the product is then deblocked at the α-amino function.

1.2.b) 7-{N^α-[O-(3-O-Carboxymethyl-β-L-fucopyranosyl)-4-hydroxy-phenylamino-thiocarbonyl]-N^ε-[fluorenyl-9-methoxycarbonyl]-L-lysyl-L-alanyloxymethyl}-camptothecin The compound from Example 1.2.a is reacted by the method of Example 1.1 with 1.2 equivalents of the carbohydrate derivative from Example I.2.

1.2) 7-{N^α-[O-(3-O-Carboxymethyl-β-L-fucopyranosyl)-4-hydroxy-phenylamino-thiocarbonyl]-L-lysyl-L-alanyloxymethyl}-camptothecin, hydrochloride The conjugate 1.2.b is deblocked with piperidine in DMF. After 30 minutes the mixture is concentrated and the residue is digested twice with dichloromethane. It is then taken up in DMF and precipitated from methanol/ether. The product is filtered off with suction, washed with ether and then lyophilized from dioxane/water. The lyophilizate is subsequently taken up in water, 1 equivalent of a 0.01N HCl solution is added, and lyophilization is repeated.

Example 1.3

7-{N^α-[O-(3-O-Carboxymethyl-β-L-fucopyranosyl)-4-hydroxy-phenylamino-thiocarbonyl]-L-lysyl-L-valyloxymethyl}-camptothecin, hydrochloride The compound is prepared by the method of Example 1.2, with 7-hydroxymethyl-camptothecin having been acylated beforehand with N-tert-butoxycarbonyl-L-valine-N-carboxyanhydride by the method of Example 1.1.b. [TLC: acetonitrile/water/glacial acetic acid 10:3:1.5 R_f=0.3] [FAB-MS: m/z=961=M+H].

Example 1.4

7-{N^α-[O-(3-O-Methyl-β-L-fucopyranosyl)-4-hydroxy-phenylamino-thiocarbonyl)-L-lysyl-L-valyoxymethyl}-camptothecin, Hydrochloride The compound is prepared by the method of Example 1.3. The carbohydrate component employed is the compound from Example 1.1 instead of that from Example 1.2 [TLC: acetonitrile/water/glacial acetic acid 5:1:0.2 R_f=0.34].

Example 2.1

9-{N^α,N^ε-bis-[O-(3-O-Methyl-β-L-fucopyranosyl)-4-hydroxy-phenylamino-thiocarbonyl]-L-lysyl-L-alanyl-amino}-camptothecin

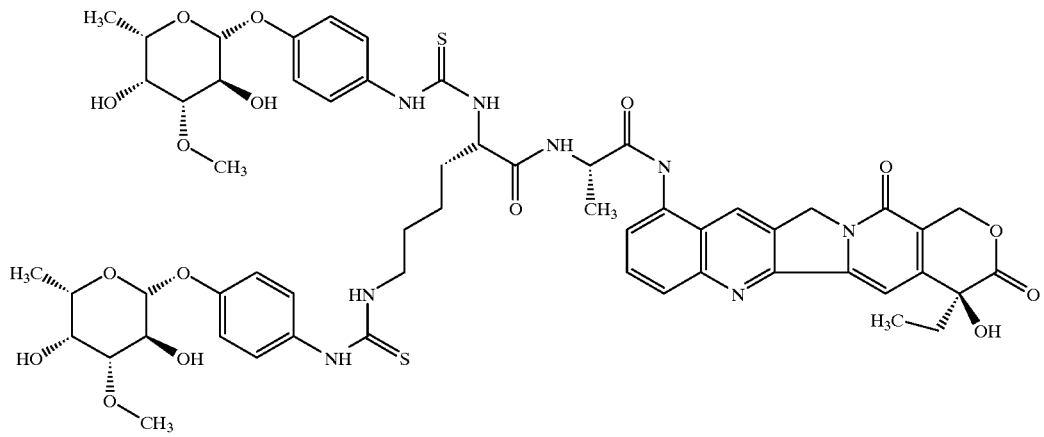

2.1.a) 9-Amino-camptothecin

Preparation is carried out in accordance with the procedure of Wani et al. (J. Med. Chem. 29 (1986), 2358).

2.1.b) 9-[L-alanyl-amino]-camptothecin

N-(Fluorenyl-9-methoxycarbonyl)-L-alanine (0.28mmol) is converted to the acid chloride in a conventional manner using thionyl chloride. This acid chloride is added after brief drying under inert gas to a solution of 0.14 mmol of the compound 2.1.a and 17 μl of pyridine in 20 ml of absolute dichloromethane. After stirring at room temperature for 16 h the mixture is concentrated, the residue is taken up in DMF, and 500 mg of Celite are added. The solvent is evaporated off and the material bound to Celite is placed on a flash column packed with silica gel. It is subsequently chromatographed with 5% methanol in dichloromethane. The corresponding fractions are collected and concentrated and the residue is digested with ether. Drying gives the Fmoc-protected intermediate in a yield of 59%. The product is taken up in 5 ml of DMF, and 250 μl of piperidine are added in order to detach the Fmoc protective group. After 20 minutes of stirring at room temperature the product is concentrated and the target compound is precipitated from dichloromethane with ether. It is obtained in quantitative yield [DC: acetonitrile/water/glacial acetic acid 5:1:0.2 $R_f$=0.2].

2.1.c) 9-(L-Lysyl-L-alanyl-amino)-camptothecin, bis-trifluoroacetate 100 mg of the conjugate from Example 2.1.b are coupled with $N^\alpha,N^\epsilon$-bis-(tert-butoxycarbonyl)-L-lysine by the method of Example 1.1.c and the product is subsequently deblocked with trifluoroacetic acid. The target compound is obtained in a total yield of 75%. [TLC: acetonitrile/water/glacial acetic acid 10:5:3 $R_f$ 0.19] [FAB-MS: m/z=563=M+H].

2.1) 9-($N^\alpha,N^\epsilon$-bis-[O-(3-O-Methyl-β-L-fucopyranosyl)-4-hydroxy-phenylamino-thiocarbonyl]-L-lysyl-L-alanyl-amino}-camptothecin The desired glycoconjugate is prepared by the method of Example 1.1 by coupling the peptide conjugate 2.1.c with the carbohydrate derivative from Example I.1. Yield: 60% [TLC: Acetonitrile/water 10:1 $R_f$=0.33] [FAB-MS: m/z= 1185 M+H].

Example 2.2

9-{$N^\alpha$-[O-(3-O-Carboxymethyl-β-L-fucopyranosyl)-4-hydroxy-phenylamino-thiocarbonyl]-L-lysyl-L-alanyl-amino}-camptothecin, hydrochloride

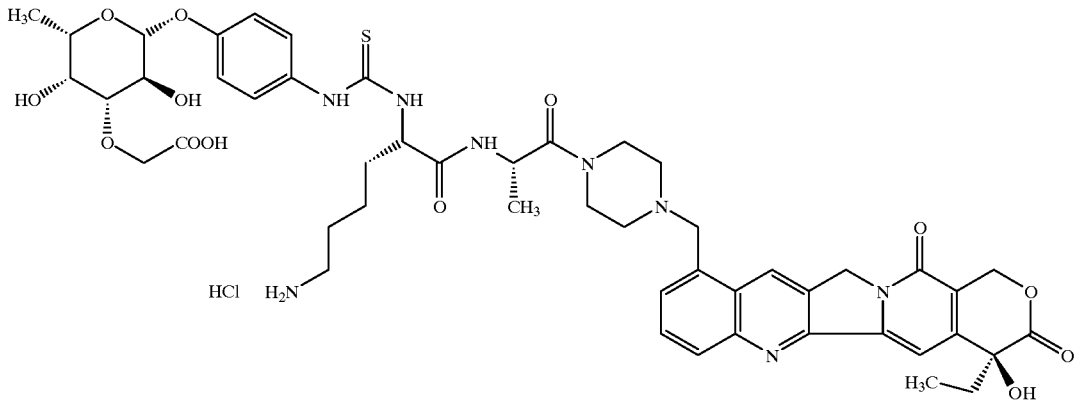

This conjugate is prepared from the L-alanyl conjugate in Example 2.1.b by the method of Examples 1.2.a, 1.2.b and 1.2.

Example 2.3

9-{$N^\alpha$-[O-(3-O-Carboxymethyl-β-L-fucopyranosyl)-4-hydroxy-phenylamino-thiocarbonyl]-L-lysyl-L-valyl-amino}-camptothecin, hydrochloride The compound is prepared by the method of Example 2.2.

Example 3.1

10,11-(Ethylenedioxy)-7-{1-[($N^\alpha,N^\epsilon$-bis-(O-(3-O-methyl-β-L-fucopyranosyl)-4-hydroxy-phenylamino-thiocarbonyl)-L-lysyl-L-alanyl]-piperazino-4yl-methyl}-20(R/S)-camptothecin

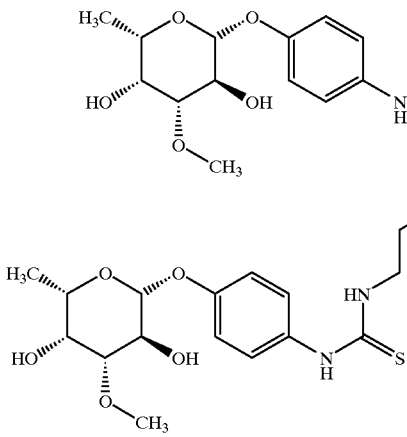
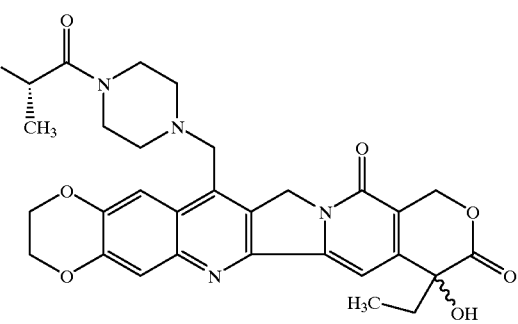

3.1.a) 7-(Chloromethyl)-10,11-(ethylenedioxy)-20 (R/S)-camptothecin

This compound is prepared from the racemic tricyclic compound, in analogy to the 20(S) compound, in accordance with the procedure of Luzzio et al. (J.Med.Chemn. 38 (1995), 395).

3.1.b) N-(tert-Butoxycarbonyl-L-alanyl)-piperazine 1.15 g of the N-hydroxysuccinimide ester of N-(tert-butoxycarbonyl)-L-alanine are dissolved in 100 ml of DMF and the solution is added dropwise over 6 hours to a mixture of 3.4 g (10 equivalents) of piperazine in 200 ml of DMF. The mixture is concentrated and the residue is taken up in water and extracted three times with 200 ml of dichloromethane each time. The organic phase is dried and the solvent is removed under reduced pressure. The target compound is obtained in a yield of 88%. [TLC: acetonitrile/water/glacial acetic acid 5:1:0.2 $R_f=0.42$].

3.1.c) 10,11-(Ethylenedioxy)-7-{1-[L-alanyl]-piperazin-4-yl-methyl}-20(R/S)-camptothecin, trifluoroacetate 125 mg (0.485 mmol) of the Compound 3.1.b are taken up in 2 ml of DMF and the mixture is added dropwise at 50° C. to a solution of 100 mg (0.22 mmol) of 3.1.a in 10 ml of DMF. This mixture is heated to room temperature and stirred for 16 h. Subsequently, the product formed is purified by flash chromatography on silica gel with dichloromethane/methanol 98:2 and subsequently 96:4. Concentration of the corresponding fractions gives the protected intermediate in a yield of 44%. [TLC: dichloromethane/methanol 95:5 $R_f=0.3$]. Elimination of the Boc protective group in accordance with standard conditions using trifluoroacetic acid in dichloromethane gives the target compound in a virtually quantitative yield [TLC: acetonitrile/water/glacial acetic acid 5:1:0.2 $R_f=0.16$] [FAB-MS: m/z=576=M+H].

3.1.d) 10,11-(Ethylenedioxy)-7-{1-[L-lysyl-L-alanyl]-piperazin-4-yl-methyl}-20(R/S)-camptothecin, bis-trifluoroacetate 50 mg of the conjugate from Example 3.1.c are added to a solution of 31 mg (0.088 mmol) of $N^\alpha,N^\epsilon$-bis-(tert-butoxycarbonyl-L-lysine, 18 mg of N-hydroxybenzotriazole and 20 mg of N-ethyl-N'-(3-dimethylaminopropyl)-carbodiimide hydrochloride in 5 ml of DMF and the mixture is stirred at room temperature for two hours. It is concentrated and the residue is stirred up with water. The product obtained is subsequently taken up in 5 ml of dichloromethane, 500 μml of trifluoroacetic acid are added at 0° C., and the mixture is stirred at room temperature for one hour. After concentration, the residue is stirred up with ether and the product is precipitated with dichloromethane/ether. The target compound is obtained in a total yield of 52%. [TLC: acetonitrile/water/glacial acetic acid 10:5:3 $R_f=0.15$].

3.1) 10,11-(Ethylenedioxy)-7-{1-[($N^\alpha,N^\epsilon$-bis-(O-(3-O-methyl-β-L-fucopyranosyl)-4-yl-hydroxyphenylamino-thiocarbonyl)-L-lysyl-L-alanyl]-piperazin-4-yl-methyl}-20(R/S)-camptothecin The desired glycoconjugate is prepared by the method of Example 1.1 by coupling the peptide conjugate 3.1.d with the carbohydrate derivative from Example I.1. Yield: 77% (TLC: acetonitrile/water 10:1 $R_f=0.31$) [FAB-MS: m/z=1326=M+H].

Example 3.2

10,11-(Ethylenedioxy)-7-{1-[($N^\alpha,N^\epsilon$-bis-(O-(3-O-methyl-β-L-fucopyranosyl)-4-yl-hydroxyphenylamino-thiocarbonyl)-L-lysyl-L-alanyl]-piperazin-4-yl-methyl}-20(S)-camptothecin This product is prepared in a manner completely analogous to that of the 20-(R/S) mixture in Example 3.1, from the enantiomerically pure S-configured tricyclic compound.

Example 3.3

10,11-(Ethylenedioxy)-7-{1-[$N^\alpha$-(O-(3-O-carboxymethyl-β-L-fucopyranosyl)-4-hydroxyphenylaminothiocarbonyl]-L-lysyl-L-alanyl]-piperazin-4-yl-methyl}-20(R/S)-camptothecin, hydrochloride

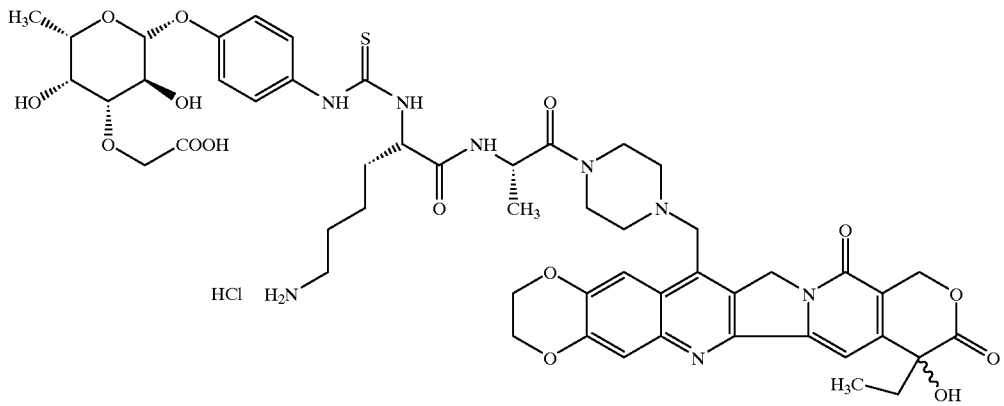

This conjugate is prepared by the method of Examples 1.2.a, 1.2.b and 1.2 from the L-alanyl conjugate in Example 3.1.c.

Example 3.4

10,11-(Ethylenedioxy)-7-{1-N$^\alpha$-(O-(3-O-carboxymethyl-β-L-fucopyranosyl)4-hydroxy-phenylamino-thiocarbonyl]-L-lysyl-L-valyl]-piperazin-4-yl-methyl}-20(R/S)-camptothecin, hydrochloride The compound is prepared by the method of Example 3.3.

Example 3.5

10,11-(Ethylenedioxy)-7-{1-[N$^\alpha$-(O-(3-O-methyl-β-L-fucopyranosyl)-4hydroxy-phenylamino-thiocarbonyl]-L-lysyl-L-alanyl]-piperazin-4-yl-methyl}-20(R/S)-camptothecin, hydrochloride This conjugate is prepared by the method of Example 3.3 using the carbohydrate from Example I.1. [TLC: acetonitrile/water/glacial acetic acid 10:3:1.5 R$_f$=0.48].

Example 4.1

10,11-(Ethylenedioxy)-7-{[N$^\alpha$-(O-(3-O-methyl-β-L-fucopyranosyl)-4-hydroxy-phenylamino-thiocarbonyl]-L-lysyl-L-alanyl]-aminomethyl}-20(S)-camptothecin, hydrochloride

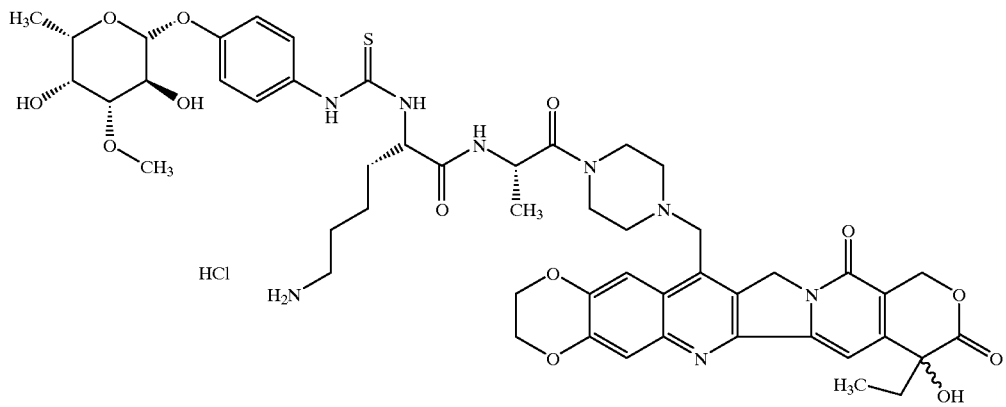

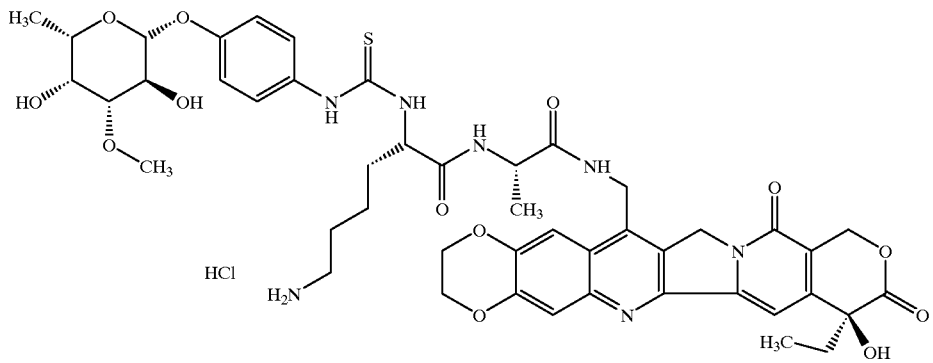

4.1.a) 10,11-(Ethylenedioxy)-7-aminomethyl-20(S)-camptothecin

This compound is prepared in accordance with the procedures of Luzzio et al. (EP 540099). Yield: 32% [TLC: dichloromethane/methanol 5:1 $R_f$=0.33].

4.1.b) 10/11-(Ethylenedioxy)-7-(L-alanyl-aminomethyl]-20(S)-camptothecin 0.275 mmol of the compound from Example 4.1.a and 0.55 mmol of ethyl-diisopropylamine are added to N-(tert-butoxycarbonyl)-L-alanine-N-hydroxy-succinimide ester (0.275 mmol) in 10 ml of dimethylformamide. After stirring at room temperature for 2 h the mixture is concentrated and the residue is precipitated from dichloromethane/methanol (1:1) with ether. Reprecipitation gives the Boc-protected intermediate in a yield of 70%. The product is taken up in 10 ml of dichloromethane, and 2 ml of anhydrous trifluoroacetic acid are added in order to detach the Boc protective group. After stirring at room temperature for 30 minutes, the mixture is concentrated and the target compound is precipitated from dichloromethane/methanol with ether. The residue is taken up in water and extracted by shaking with dichloromethane. Following concentration of the aqueous phase, the product is reprecipitated from dichloromethane/methanol with ether. Yield: 69% [TLC: acetonitrile/water/glacial acetic acid 5:1:0.2 $R_f$=0.25] [FAB-MS: m/z=507=M+H].

4.1.c) 10,11-(Ethylenedioxy)-7-[N$^\epsilon$-(fluorenyl-9-methoxycarbonyl)-L-lysyl-L-alanyl-aminomethyl]-camptothecin, trifluoroacetate The conjugate from Example 4.1.b is linked to N$^\alpha$-(tert-butoxycarbonyl)-N$^\epsilon$-(fluorenyl-9-methoxycarbonyl)-L-lysine in accordance with standard procedure and is subsequently deblocked at the α-amino function.

4.1.d) 10,11-(Ethylenedioxy)-7-{[N$^\alpha$-(O-(3-O-methyl-β-L-fucopyranosyl)-4-hydroxy-phenylamino-thiocarbonyl]-N$^\epsilon$-[fluorenyl-9-methoxycarbonyl]-L-lysyl-L-alanyl-aminomethyl}-20(S)-camptothecin The compound from Example 4.1.c is reacted with 1.2 equivalents of the carbohydrate derivative from Example I.1 by the method of Example 1.1. Yield: 83%.

4.1) 10,11-(Ethylenedioxy)-7-{[N$^\alpha$-(O-(3-O-methyl-β-L-fucopyranosyl)-4-hydroxy-phenylamino-thiocarbonyl]-L-lysyl-L-alanyl-aminomethyl}-20(S)-camptothecin, hydrochloride The conjugate 4.1.d is deblocked with piperidine in DMF. After 30 minutes the mixture is concentrated and the product is precipitated twice from dichloromethane/methanol with ether. It is subsequently taken up in water, 1 equivalent of an 0.01 N HCl solution is added, and the product is lyophilized. Yield: 69% [TLC: acetonitrile/water/glacial acetic acid 10:3:1.5 $R_f$=0.39] [ESI-MS: m/Z=946=M+H].

What is claimed is:

1. Compounds of the formula (I)

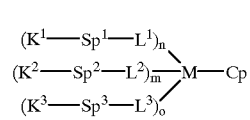

in which n, m and o in each case represent the number 0 or 1 and n+m+o is ≧1 where Cp represents a camptothecin radical of the formulae

[A]

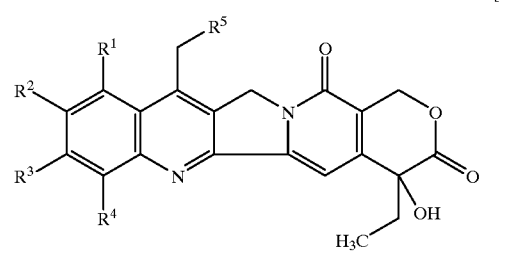

in which $R^1$, $R^2$, $R^3$ and $R^4$ independently of one another may represent hydrogen, alkyl having up to 3 carbon atoms, halogen, amino, hydroxyl or nitro or $R^2$ and $R^3$ together represent a group of the formula

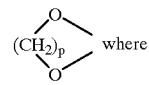

p may have the values 1 or 2 and $R^5$ represents —O—*, —NH* or

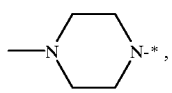

or represents —*$NR^6$, in which $R^6$ represents arylmethyl or hetarylmethyl,

[B]

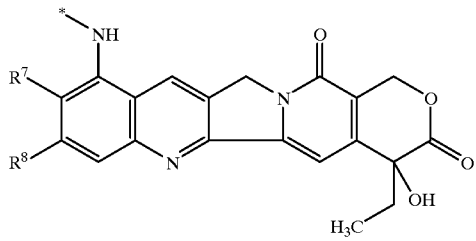

in which
$R^7$ and $R^8$ are as defined for $R^2$ and $R^3$ and may be identical or different to these,

[C]

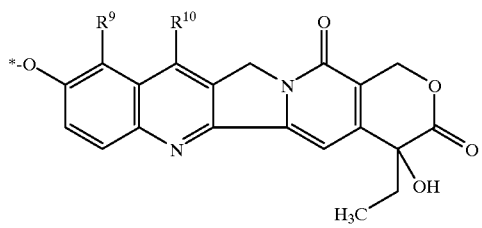

in which
$R^9$ represents hydrogen or —$CH_2$—$N(CH_3)_2$ and
$R^{10}$ represents hydrogen or ethyl,

[D]

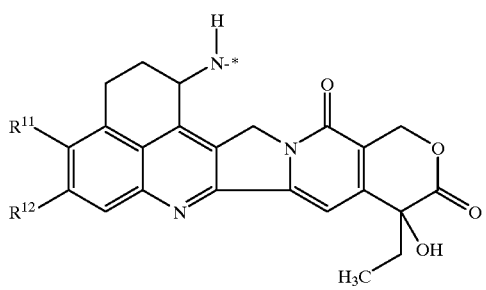

in which
$R^{11}$ and $R^{12}$ are as defined for $R^2$ and $R^3$ and may be identical or different to these, or

[E]

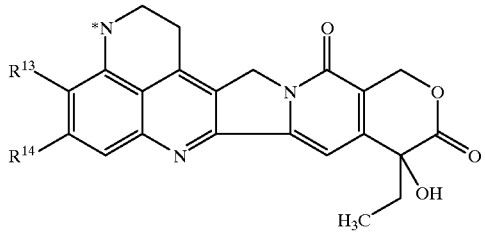

in which
$R^{13}$ and $R^{14}$ are as defined for $R^2$ and $R^3$ and may be identical or different to these,
where Cp is attached to M via the bonds labelled *,
M represents a bridge grouping whose main chain includes up to 21 atoms in linear order,
$L^1$, $L^2$ and $L^3$ independently of one another each represent linker groupings,
$Sp^1$, $Sp^2$ and $Sp^3$ independently of one another each represent arylene having up to 10 carbon atoms or represent alkylene having up to 8 carbon atoms which are in each case optionally substituted, and
$K^1$, $K^2$ and $K^3$ independently of one another each represent a radical of the formula (II)

(II)

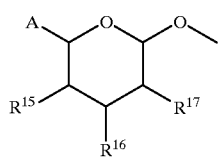

in which
A represents methyl, hydroxymethyl, alkoxymethyl having up to 6 carbon atoms, acyloxymethyl having up to 6 carbon atoms or a radical of the formula —$CH_2$—B in which
B represents a radical of the formula (II),
$R^{15}$, $R^{16}$ and $R^{17}$ independently of one another each represent hydrogen, hydroxyl, optionally hydroxyl-substituted alkoxy having up to 6 carbon atoms, amino which is optionally substituted by alkyl or acyl having up to 6 carbon atoms, halogen, sulphate or a group of the formula

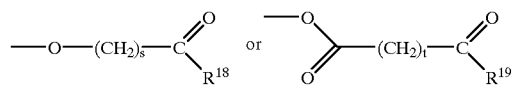

in which
$R^{18}$ and $R^{19}$ independently of one another each represent hydroxyl or alkoxy having up to 6 carbon atoms or represent amino which is optionally substituted by alkyl having up to 6 carbon atoms, and
s and t independently of one another may each have the values 0, 1, 2, 3 or 4, or $R^{15}$, $R^{16}$ and $R^{17}$ independently of one another each represent a radical of the formula (II) or two of the radicals $R^{15}$, $R^{16}$, $R^{17}$ together represent an epoxy group, and their isomers, isomer mixtures and salts.

2. Compounds of the formula (I) according to claim 1, in which $K^1$, $K^2$ and $K^3$ independently of one another may each represent a radical of the formula (II) where A represents methyl, hydroxymethyl, methoxymethyl or acetoxymethyl, $R^{15}$ represents hydrogen, hydroxyl, methoxy or a group of the formula $$-O-(CH_2)_s-C\begin{matrix}O\\R^{18}\end{matrix} \quad \text{or} \quad \begin{matrix}-O\\O\end{matrix}-(CH_2)_t-C\begin{matrix}O\\R^{19}\end{matrix}$$

in which s and t independently of one another may each have the values 1 or 2 and $R^{18}$ and $R^{19}$ independently of one another each represent hydroxyl or alkoxy having up to 4 carbon atoms, or $R^{15}$ represents a radical of the formula (II), $R^{16}$ represents hydrogen, hydroxyl, halogen, alkoxy having up to 4 carbon atoms, sulphate or a group of the formula $$-O-(CH_2)_s-C\begin{matrix}O\\R^{18}\end{matrix} \quad \text{or} \quad \begin{matrix}-O\\O\end{matrix}-(CH_2)_t-C\begin{matrix}O\\R^{19}\end{matrix}$$

in which s and t independently of one another may each have the values 1 or 2 and $R^{18}$ and $R^{19}$ independently of one another each represent hydroxyl or alkoxy having up to 4 carbon atoms or represent amino which is optionally substituted by alkyl having up to 4 carbon atoms, $R^{17}$ represents hydroxyl, alkoxy having up to 4 carbon atoms which is optionally substituted by hydroxyl, amino which is optionally substituted by alkyl or acyl having up to 4 carbon atoms, or a group of the formula $$-O-(CH_2)_s-C\begin{matrix}O\\R^{18}\end{matrix} \quad \text{or} \quad \begin{matrix}-O\\O\end{matrix}-(CH_2)_t-C\begin{matrix}O\\R^{19}\end{matrix}$$

in which s and t independently of one another may each have the values 1 or 2 and $R^{18}$ and $R^{19}$ independently of one another each represent hydroxyl or alkoxy having up to 4 carbon atoms, or in which $R^{15}$ and $R^{16}$ together represent an epoxy group, and their isomers, isomer mixtures and salts.

3. Compounds of the formula (I) according to claim 1 in which $Sp^1$, $Sp^2$ and $Sp^3$ independently of one another may each represent arylene having up to 10 carbon atoms which is attached to in each case one group $K^1$ and/or $K^2$ or $K^3$ and $L^1$ and/or $L^2$ or $L^3$ and which is optionally also mono- or polysubstituted by hydroxyl, carboxyl, carboxyalkyl having up to 4 carbon atoms, nitro, cyano, halogen, alkyl having up to 4 carbon atoms, halogenoalkyl having up to 4 carbon atoms, alkoxy having up to 4 carbon atoms, and their isomers, isomer mixtures and salts.

4. Compounds of the formula (I) according to claim 1 in which $L^1$, $L^2$ and $L^3$ independently of one another each represent $$-NH-\overset{S}{\underset{\|}{C}}-\text{,}$$

$$-NH-\overset{O}{\underset{\|}{C}}-\text{,} \quad -\overset{O}{\underset{\|}{C}}- \quad \text{or}$$

$$-HN-\underset{\underset{N}{\|}}{\overset{R^{20}}{\underset{N}{\|}}}\!\!\!\!\!\!\!\!\!\!\!\!\!\!\!\!\!\!\!\!\!\!\!\!\! \text{where}$$

$R^{20}$ represents chlorine or represents hydroxyalkylamino having up to 6 carbon atoms, and their isomers, isomer mixtures and salts.

5. Compounds of the formula (I) according to claim 1 in which

M represents a peptide which is attached to $L^1$, $L^2$ and/or $L^3$ via an amino function, is attached to Cp via an acyl function and whose amino acid building blocks may optionally carry protective groups, and their isomers, isomer mixtures and salts.

6. Compounds according to claim 5, wherein M represents a mono-, di- or tripeptide.

7. Compounds according to claim 5, wherein the peptide comprises amino acid building blocks selected from the group consisting of glycyl, alanyl, valyl, leucyl, lysyl, seryl, glutamyl, threonyl, asparagyl, isoleucyl, diaminopropionyl, diaminobutyryl, histidyl, arginyl and/or ornithyl which optionally carry protective groups.

8. Process for preparing compounds of the formula (I) according to claim 1, wherein compounds of the formula (III)

$$Cp-H \qquad \qquad (III)$$

in which Cp is as defined according to claim 1 and the hydrogen atom is located on the positions labelled *, are reacted with an activated carboxyl component Ma which corresponds to the radical M defined according to claim 1 and optionally carries protective groups, in a suitable solvent, optionally in the presence of a base, one, more than one or all protective groups of M are, optionally, selectively removed and the product is reacted with compounds of the formula (IV)

$$K^1-Sp^1-L^1a \qquad \qquad (IV)$$

in which $K^1$ and $Sp^1$ are each as defined according to claim 1 and $L^1a$ represents a reactive precursor of the group $L^1$, where the protective groups are, optionally, selectively removed and various groups of $K^2-Sp^2-L^2-$ and $K^3-Sp^3-L^3-$ can be introduced stepwise in a comparable manner, or that, if M is a peptide, a first amino acid radical is introduced in a comparable manner in the form of a corresponding activated carboxyl component which optionally carries protective groups, protective groups are, optionally removed and amino acid radicals which optionally carry protective groups are furthermore attached, radicals of the formulae $K^1$—$Sp^1$—$L^1$—, $K^2$—$Sp^2$—$L^2$— and/or $K^3$—$Sp^3$—$L^3$— are introduced and, optionally, protective groups are removed, that furthermore, optionally, the stereoisomers are separated and that the compounds are, optionally, converted into their salts.

9. A pharmaceutical composition comprising at least one compound, isomer, isomer mixture or salt according to claim 1 and a non-toxic, inert pharmaceutically suitable excipient.

10. A method of treating a tumor in a patient suffering therefrom, said method comprising administering to said patient an effective amount therefor of at least one compound, isomer, isomer mixture or salt according to claim 1.

* * * * *